US009156709B2

(12) United States Patent
Shallcross

(10) Patent No.: US 9,156,709 B2
(45) Date of Patent: Oct. 13, 2015

(54) MULTI-ROTATOR MAGNETIC RESONATOR EMBODYING SACRED GEOMETRY

(76) Inventor: Kim Shallcross, Milton (CA)

( * ) Notice: Subject to any disclaimer, the term of this patent is extended or adjusted under 35 U.S.C. 154(b) by 1186 days.

(21) Appl. No.: 12/096,063

(22) PCT Filed: Dec. 6, 2006

(86) PCT No.: PCT/CA2006/001984
§ 371 (c)(1),
(2), (4) Date: Jun. 4, 2008

(87) PCT Pub. No.: WO2007/065257
PCT Pub. Date: Jun. 14, 2007

(65) Prior Publication Data
US 2008/0296162 A1 Dec. 4, 2008

(30) Foreign Application Priority Data
Dec. 6, 2005 (CA) .................. 2526977

(51) Int. Cl.
C02F 1/48 (2006.01)
C02F 1/00 (2006.01)
A61N 2/06 (2006.01)
A61N 2/12 (2006.01)
H01F 7/02 (2006.01)

(52) U.S. Cl.
CPC . *C02F 1/005* (2013.01); *A61N 2/06* (2013.01); *A61N 2/12* (2013.01); *C02F 1/481* (2013.01); *H01F 7/0294* (2013.01)

(58) Field of Classification Search
CPC ............ C02F 1/005; C02F 1/48; C02F 1/481; C02F 1/482; A61N 2/06; A61N 2/12
USPC .................. 335/306; 210/222–223; 600/9
See application file for complete search history.

(56) References Cited

U.S. PATENT DOCUMENTS

| | | | |
|---|---|---|---|
| 5,942,961 A * | 8/1999 | Srail et al. ........... | 335/284 |
| 6,093,318 A | 7/2000 | Saho et al. | |
| 6,103,113 A | 8/2000 | Saho et al. | |
| 6,171,490 B1 | 1/2001 | Kim | |

(Continued)

FOREIGN PATENT DOCUMENTS

| CA | 2526977 A1 | 4/2006 |
|---|---|---|
| CA | 2488776 A1 | 6/2006 |

OTHER PUBLICATIONS

Wikipedia: Magnet Therapy, Dec. 2, 2011, pp. 1-5.*
Wikipedia: Magnetic water treatment, Dec. 2, 2011, pp. 1-4.*
Pitkänen, About Strange Effects Related to Rotating Magnetic Systems, pp. 1-13 (undated).

(Continued)

*Primary Examiner* — Ramon Barrera
(74) *Attorney, Agent, or Firm* — Harness, Dickey & Pierce, P.L.C.

(57) ABSTRACT

A magnetic resonator is provided which has a support structure and a plurality of roller assemblies mounted thereto for rotation about respective axes of rotation which are generally parallel one to another. Drive means are coupled to the roller assemblies to rotate each of the roller assemblies about its respective axis of rotation relative to the support structure. Each roller assembly houses a plurality of magnets disposed along respective axes of the roller assemblies. The plurality of magnets are grouped in a plurality of first and second arrangements with a first arrangement being interspersed between a pair of second arrangements. At least one of the first and second arrangements incorporates a pattern or shape based on sacred geometry.

11 Claims, 7 Drawing Sheets

(56) References Cited

U.S. PATENT DOCUMENTS

| | | |
|---|---|---|
| 6,208,497 B1 | 3/2001 | Seale et al. |
| 6,277,275 B1 | 8/2001 | Yoshifusa et al. |
| 6,323,647 B1 | 11/2001 | Anderson et al. |
| 7,611,626 B2 | 11/2009 | Shallcross |

OTHER PUBLICATIONS

Email from Lucas Tessaro, Jun. 22, 2012, 1 page.
Email from Lucas Tessaro, Oct. 13, 2012, 1 page.
Email from Lucas Tessaro, Nov. 26, 2012, 1 page.
Email from Lucas Tessaro, Jan. 6, 2013, 1 page.

* cited by examiner

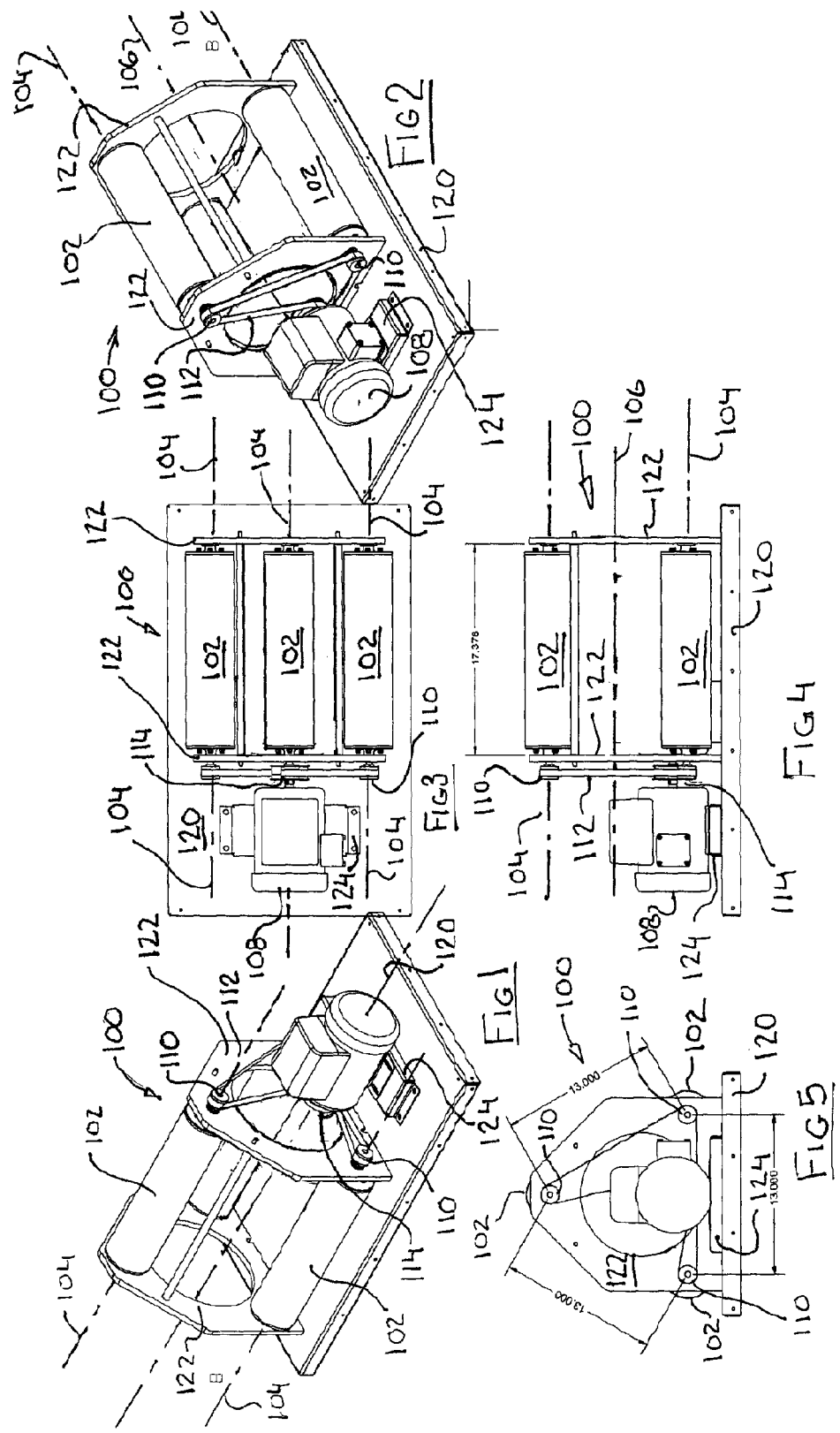

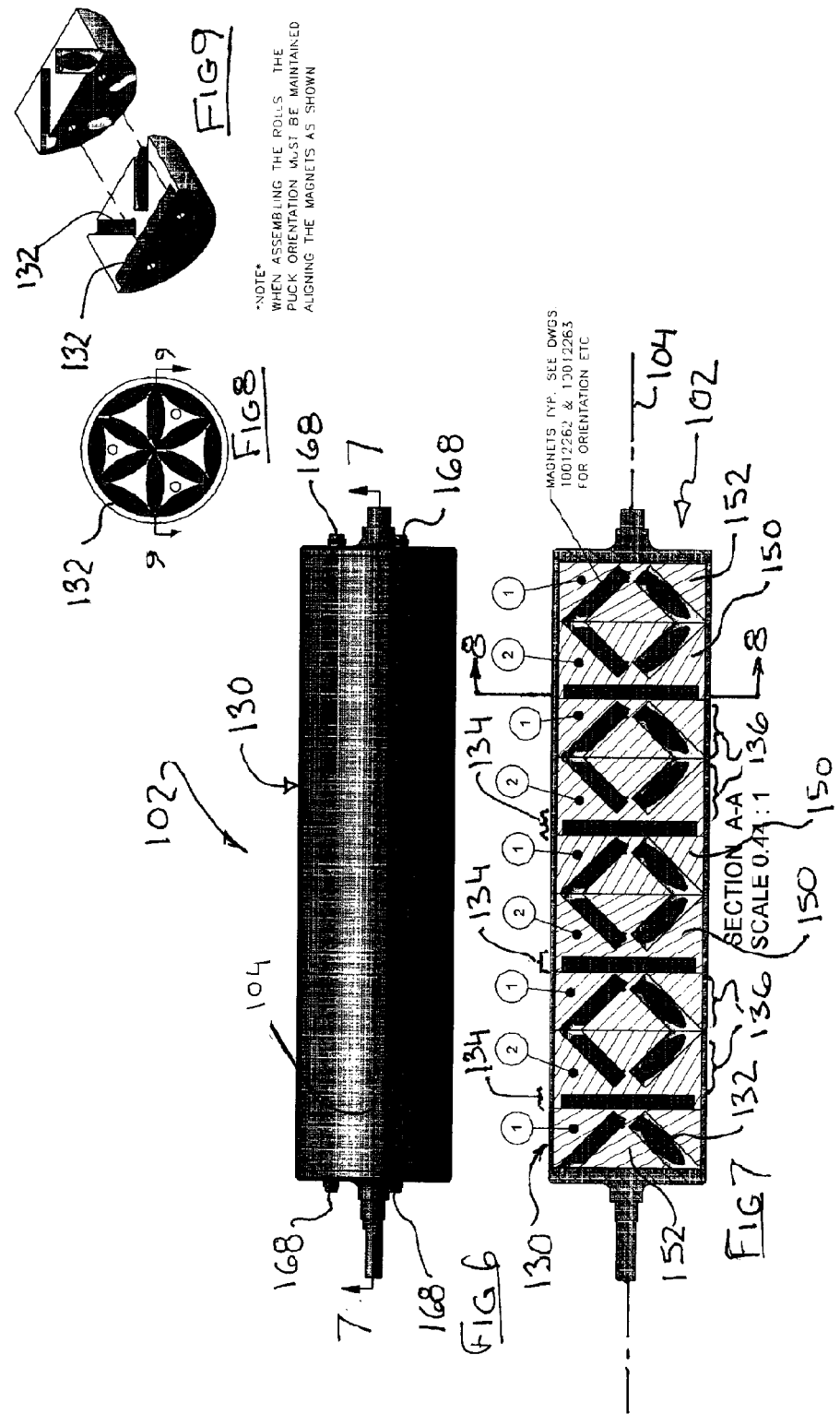

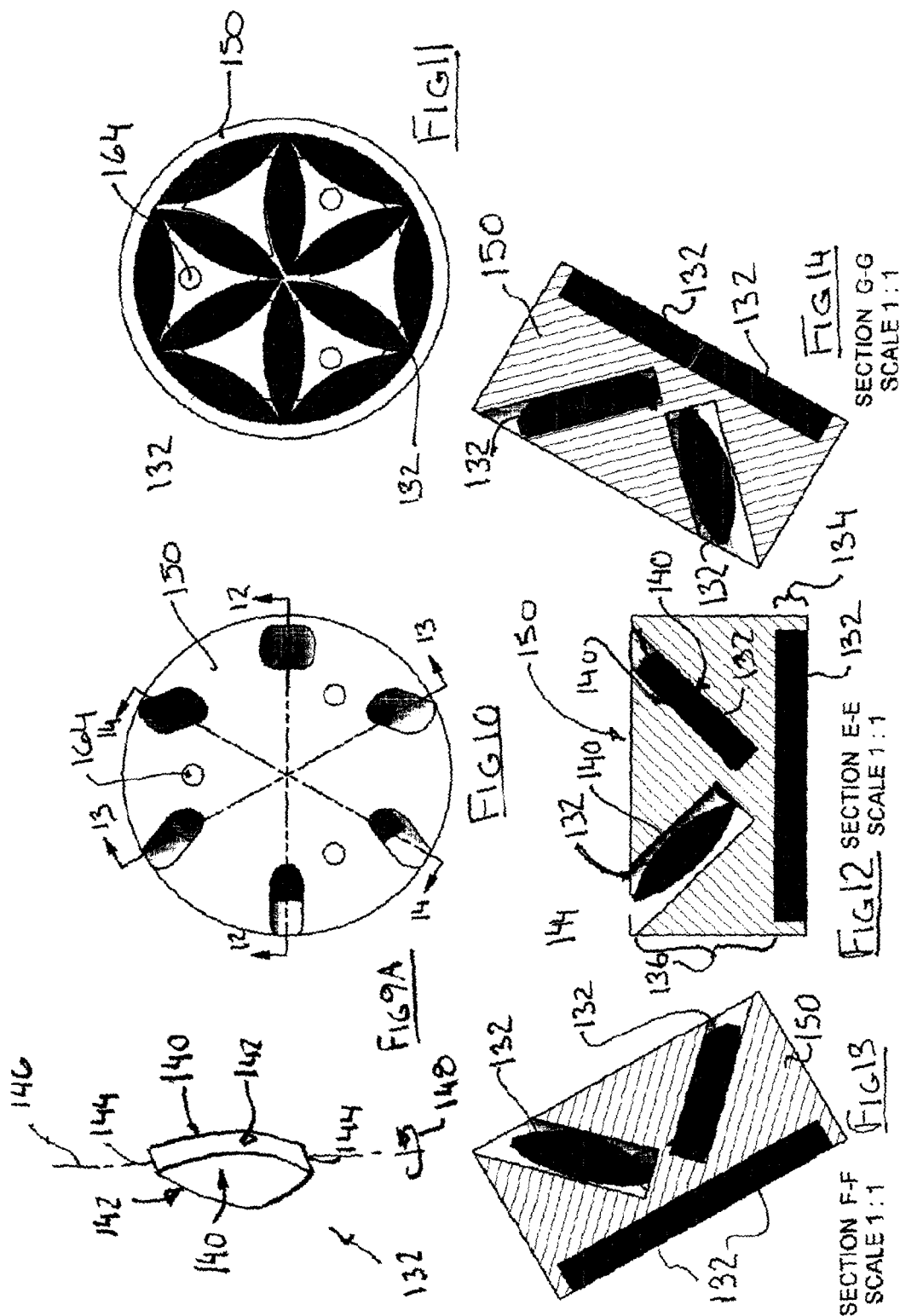

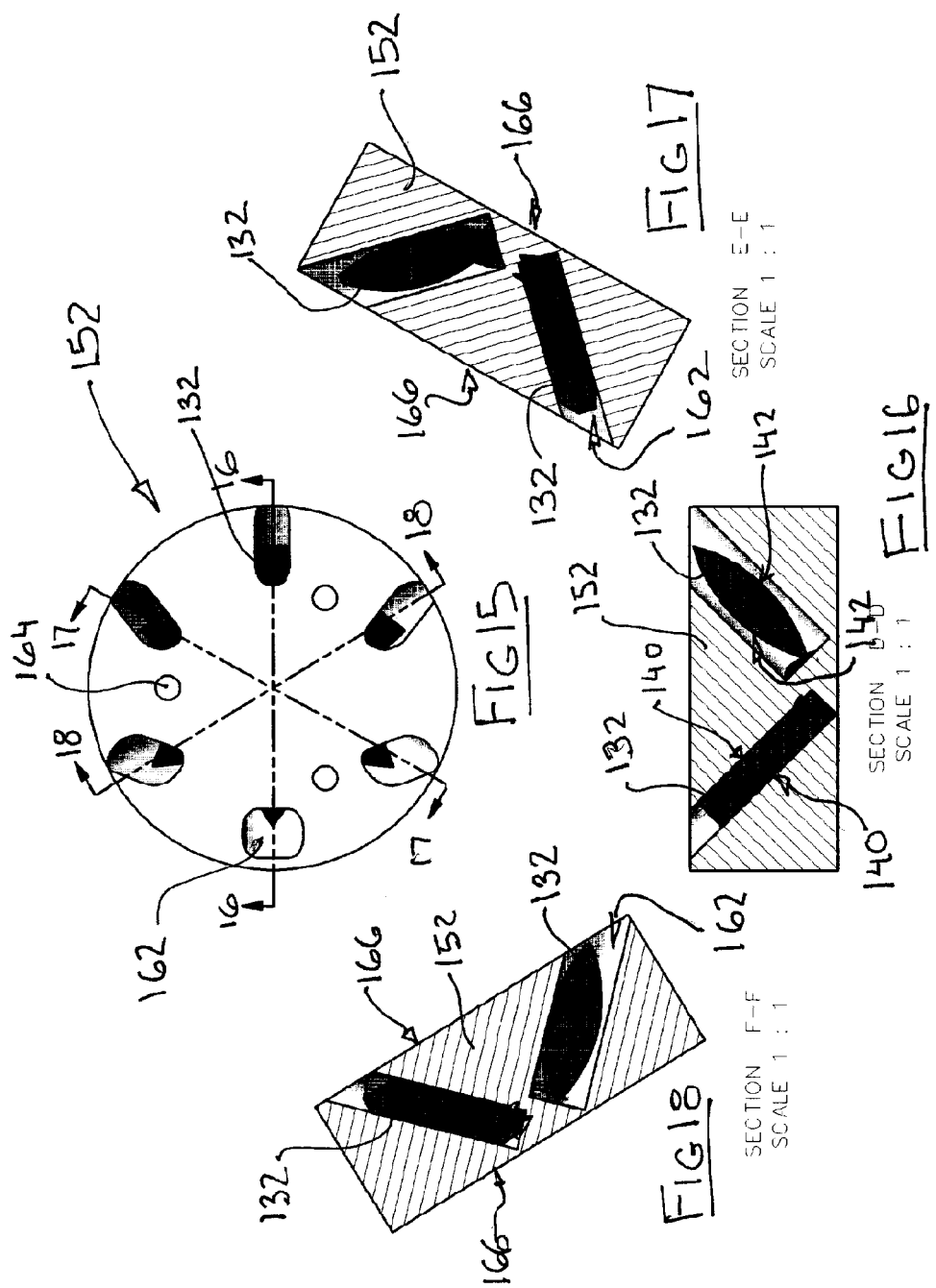

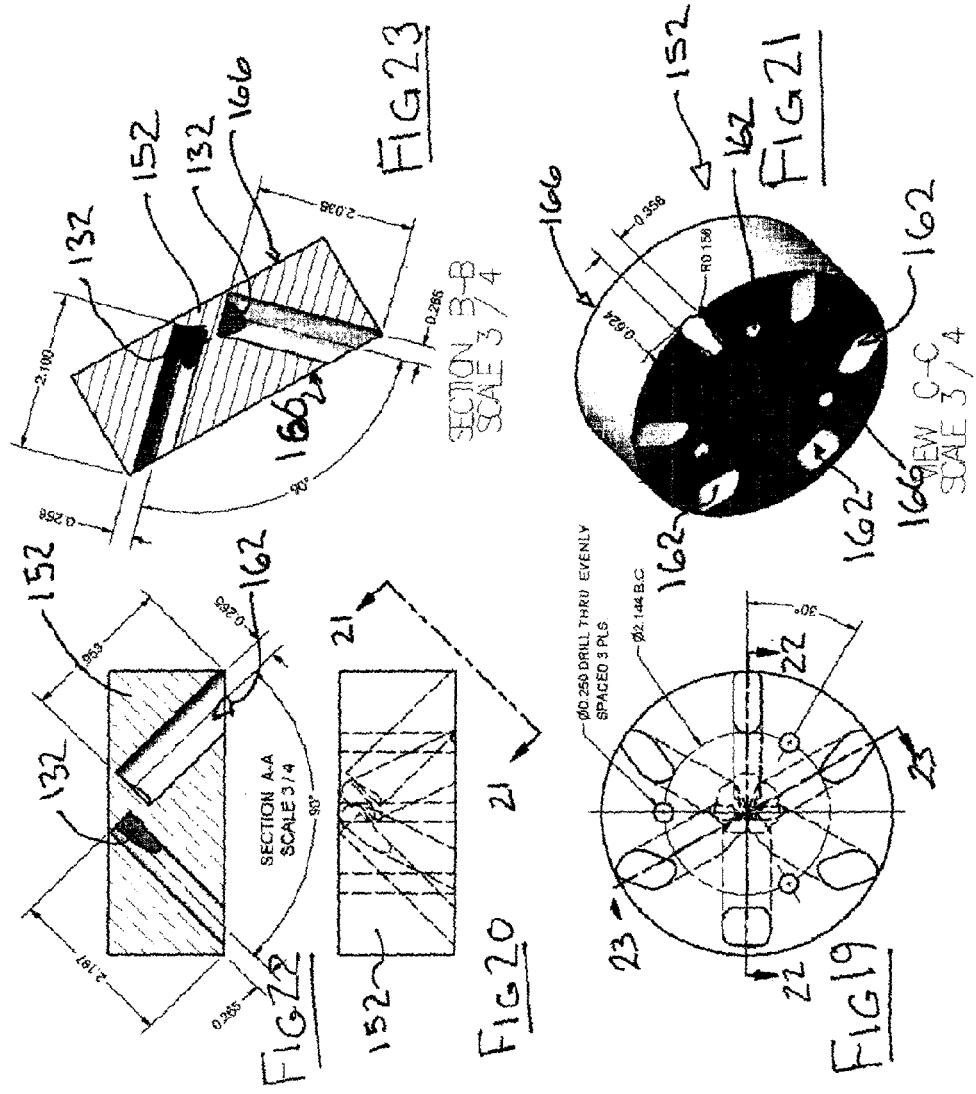

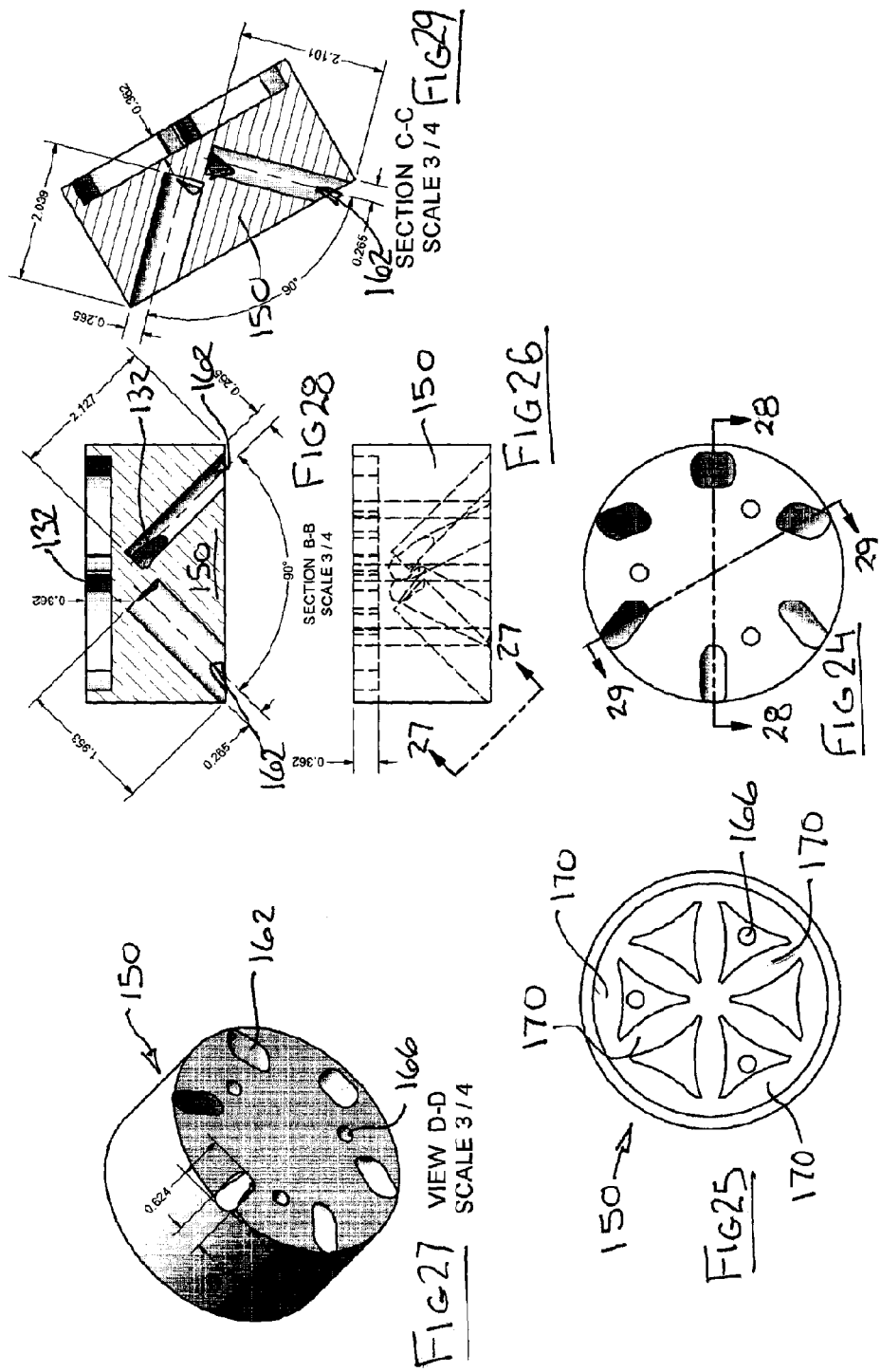

MULTI-ROTATOR MAGNETIC RESONATOR EMBODYING SACRED GEOMETRY

CROSS-REFERENCE TO RELATED APPLICATION

This application is the U.S. national phase of PCT Appln. No. PCT/CA2006/001984 filed Dec. 6, 2006, which claims priority to Canadian application 2,526,977 filed Dec. 6, 2005.

FIELD OF THE INVENTION

The present invention relates to devices that utilize magnetic fields arising from the rotation of magnets, which devices may be useful in the field of purification and healing.

BACKGROUND OF THE INVENTION

A variety of devices have been proposed for the purpose of purifying water through the use of magnetic fields. Most purifying devices are stagnant magnets, few are rotating and require contact with one or more rotating magnets within a vessel containing the water to be purified. In contrast, Applicant has previously invented magnetic purification devices which require only that the substance to be purified be near the device. Applicant's earlier inventions are exemplified in Applicant's Canadian Patent Application Nos. 2,488,776 and 2,526,977.

Applicant's earlier inventions recognize that using a plurality of magnets arranged in patterns which conform to "sacred geometry" (which is discussed in more detail below) is significantly more effective than the simple rotation of a bar magnet. Nevertheless, despite Applicant's advances to date, there is a desire for even more efficient and compact devices for purifying such things as food, water, air and soil and direct application to human and animal body surfaces for healing.

The term "sacred geometry" does not refer to any religious significance. In contrast, the term "sacred geometry" is a well-known term of art which refers to a number of basic geometrical patterns and sequences which reoccur in nature. While some of the patterns may have been used in religious rituals because of the belief that such patterns have a fundamental connection with nature and humanity, this is not the focus of the present invention.

There are numerous publications which discuss sacred geometry. Exemplary ones include The Ancient Secret of the Flower of Life (Vol. 1 and II) by 'Drunvalo Melchizedec and the Internet (see for example http:/www.intent.com/sg) and the reader is referred to those for a more in-depth study of sacred geometry.

Very broadly, sacred geometry generally relates to patterns and figures created or embodying one of five basic geometrical ratios: Pi, $\sqrt{2}$, $\sqrt{5}$, $\sqrt{3}$, and Phi.

Pi is the ratio of the diameter of the circle to its circumference.

$\sqrt{2}$ is the length of a diagonal of a square with sides of length 1.

$\sqrt{5}$ the length of the a diagonal of a rectangle with sides of length 1 and length 2.

$\sqrt{3}$ is the length of the chord connecting the points of intersection of two circles each having a radius 1, where the circumference of each intersects the centre of the other.

Phi is $(1+\sqrt{5})/2$ and is a naturally occurring ratio prevalent in animal and plant skeletal structures. It is also referred to as the "golden ratio". Most naturally occurring fractal patterns, such as snowflakes, tree shapes and so on, follow the golden ratio.

Sacred geometrical patterns are patterns constructed using the sacred geometrical ratios, such as exemplified by the "Seed of Life" pattern, used in the description of preferred embodiments set out below. Other sacred geometrical shapes and patterns include, without limitation, pentagons, pentagrams, hexagrams, equilateral triangles, squares, rectangles with sides having a 2:1 ratio, vesicapisces and 3-dimensional structures such as the pyramid and the cathara grid. Other shapes, patterns and structures will be known to those versed in sacred geometry.

SUMMARY OF THE INVENTION

In very general terms, the present invention recognizes that a significantly more effective field may be realized in a magnetic resonator embodying sacred geometry by repeating a magnetic pattern based on sacred geometry axially along a rotating roller and by utilizing a plurality of rollers arranged parallel to one another.

More particularly, a magnetic resonator is provided which has a support structure and a plurality of roller assemblies mounted thereto for rotation about respective axes of rotation which are generally parallel one to another. Drive means are coupled to the roller assemblies to rotate each of the roller assemblies about its respective axis of rotation relative to the support structure. Each roller assembly houses a plurality of magnets disposed along respective axes of the roller assemblies. The plurality of magnets are grouped in a plurality of first and second arrangements with a first arrangement being interspersed between a pair of second arrangements. At least one of the first and second arrangements incorporates a pattern or shape based on sacred geometry.

The first arrangement of magnets may be a "seed of life" pattern.

The second arrangement of magnets may include a plurality of magnets disposed generally equidistantly about the respective axes of rotation in a generally pyramid or cone-shaped pattern or shape with a vertex of the pyramid or cone facing the first arrangement.

The magnets in the second arrangement may have discernible front and rear faces on opposite sides of a longitudinal axis. The magnets may be arranged with the longitudinal axes lying along the pyramid or cone shape. Each magnet may be rotated by an equal amount in a common direction from its neighbour whereby diametrically opposed magnets have their respective front and rear faces facing in generally perpendicular directions.

The magnets in the first and second arrangements may have generally planar front and rear faces joined by curved side faces which meet at opposite ends to present a lens-like profile when viewed from the front or rear faces and a generally rectangular profile when viewed from the side face, with the longitudinal axis of each lens extending through its ends.

The magnets may be mounted in support blocks having recesses formed therein for receiving and orienting the magnets.

The support blocks may be cylindrical and housed in roller assemblies comprising a tubular shell of a non-magnetic material. Retainers may be provided which act between the shell and the support blocks to constrain the support blocks against rotation relative to the shell.

The magnetic resonator may have three roller assemblies spaced equidistantly about a common axis.

The magnets may be arranged with their north and south poles alternating.

The magnetic resonator may have four first arrangements of magnets and nine second arrangements of magnets.

Each second arrangement may include six magnets.

DESCRIPTION OF DRAWINGS

FIG. 1 is a perspective view from above showing a top, a side and an end of a magnetic resonator according to the present invention with its outer cover removed;

FIG. 2 is a view corresponding to FIG. 1 but showing the opposite side;

FIG. 3 is a top plan view of the magnetic resonator of FIGS. 1 and 2;

FIG. 4 is a front elevation corresponding to FIG. 3;

FIG. 5 is an end elevation of the magnetic resonator of FIGS. 1 and 2;

FIG. 6 is a plan or elevational view of a roller assembly of a resonator unit according to the present invention (as the roller assemblies illustrated are cylindrical, plan and elevational views would be similar);

FIG. 7 is a sectional view of the roller assembly taken on line 7-7 of FIG. 6;

FIG. 8 is a sectional view of the roller assembly of FIG. 6 corresponding to line 8-8 of FIG. 7 and showing a magnet holder according to the present invention;

FIG. 9 is a sectional view of the magnet holder of FIG. 8 taken on line 9-9 of FIG. 8;

FIG. 9A is a perspective view of a "lens" shaped magnet according to the present invention;

FIG. 10 is a front elevation of a magnet holder according to the present invention for holding 18 magnets;

FIG. 11 is a rear elevation of the magnet holder of FIG. 10;

FIG. 12 is a section on line—12-12 of FIG. 10;

FIG. 13 is a section on line 13-13 of FIG. 10;

FIG. 14 is a section on line 14-14 of FIG. 10;

FIG. 15 is a front elevation of a magnet holder according to the present invention for holding 6 magnets;

FIG. 16 is a section on line 16-16 of FIG. 15;

FIG. 17 is a section on line 17-17 of FIG. 15;

FIG. 18 is a section on line 18-18 of FIG. 15;

FIG. 19 is a front elevation showing hidden detail of a magnet holder according to the present invention for holding six (6) magnets;

FIG. 20 is a top plan view of the magnet holder of FIG. 19;

FIG. 21 is a perspective view of the magnet holder of FIGS. 19 and 20 taken from the direction of line 21-21 of FIG. 20;

FIG. 22 is a section on line 22-22 of FIG. 19;

FIG. 23 is a section on line 23-23 of FIG. 19;

FIG. 24 is a front elevation of a magnet holder according to the present invention for holding eighteen (18) magnets;

FIG. 25 is a rear elevation of the magnet holder of FIG. 24;

FIG. 26 is a top plan view of the magnet holder of FIG. 24;

FIG. 27 is a perspective view of the magnet holder of FIGS. 24, 25 and 26 taken from the perspective of line 27-27 of FIG. 26;

FIG. 28 is a section on line 28-28 of FIG. 24;

FIG. 29 is a section on line 29-29 of FIG. 24;

DESCRIPTION OF PREFERRED EMBODIMENTS

Figure 30:
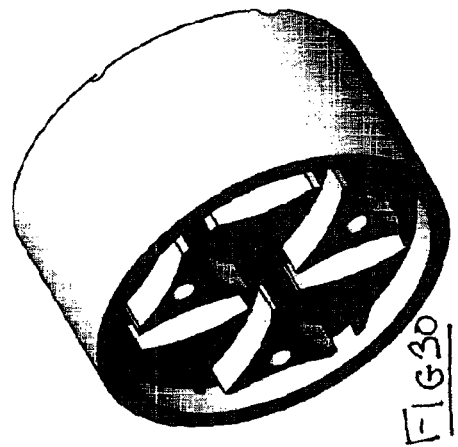
FIG. 30 is a perspective view of a magnet holder according to the present invention for holding eighteen (18) magnets.

A magnetic resonator according to the present invention is generally indicated by reference 100 in the accompanying illustrations. The magnetic resonator 100 basically comprises a plurality of roller assemblies 102, such as the cylindrical drums illustrated, mounted for rotation about respective rotational axes 104 generally parallel to each other.

The roller assemblies 102 and their respective axes are also parallel to and spaced equally about a common axis 106.

Three roller assemblies 102 are illustrated arranged with their respective axes 104 arranged to correspond to the corners of an equilateral triangle when viewed from the end, such as in FIG. 5.

A prototype magnetic resonator 100 built according to such an arrangement has provided beneficial results in testing. It is however expected that other numbers and arrangements of rollers may work. Certainly beneficial results, albeit a smaller resonant field is achievable with a single roller assembly 102.

Each of the roller assemblies 102 contains magnets arranged according to a pattern conforming to sacred geometry as described in detail further below.

The roller assemblies 102 are rotated about their respective axes 104 by any suitable motive power means or rotator to create a resonant magnetic field. A suitable rotator, as illustrated, may include a motor 108 rotatably coupled to the rotator assemblies 102 by a drive belt 112 which rides on and frictionally engages driven pulleys 110 mounted to the rotator assemblies 102. A driving pulley 114 mounted to an output shaft of the motor 108 and presses against the drive belt 112 to frictionally engage the belt 112.

It will be appreciated that the pulley and belt arrangement is exemplary and may be substituted with other drive assemblies such as a sprocket and chain assembly or a gear drive assembly, to mention but two alternatives.

The balance of the structure illustrated in FIGS. 1 through 5 is mostly support structure for the mounting and support of the components described above. The support structure illustrated includes a base 120 to which roller assembly support plates 122 are secured to extend generally perpendicularly therefrom. The roller assembly support plates would typically house bearings into which respective ends of the roller assemblies 102 are journalled for low friction rotational support. The motor 108 may be supported on the base 120 by an adjustable motor mount 122 to allow for tensioning of the drive belt 112 by moving the motor 108.

A non-magnetic cover (not illustrated) may be provided over the magnetic resonator 100 for aesthetics and to protect against inadvertent contact with any moving parts.

Figure 31:
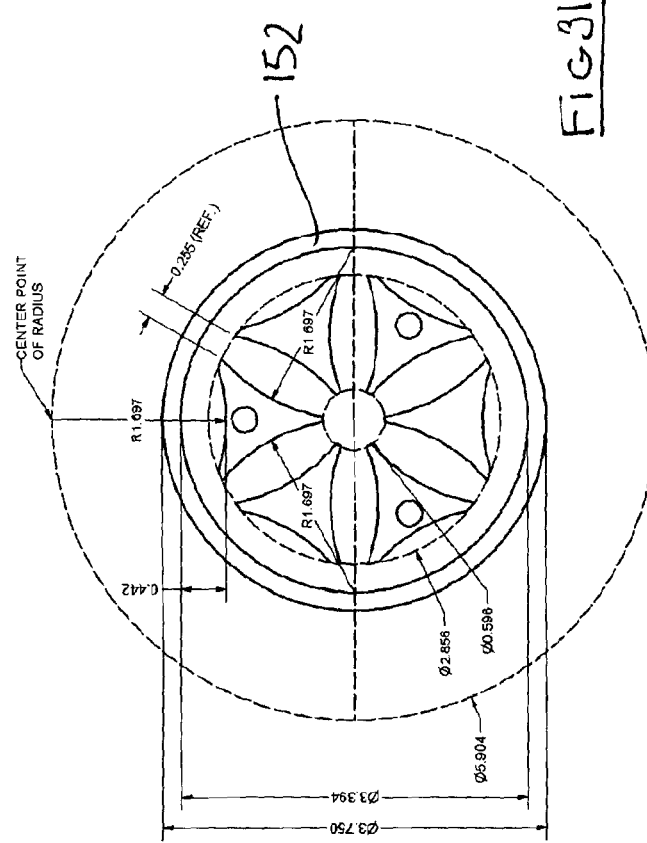
FIG. 31 is a front elevation of the magnet holder of FIG. 30 showing representative radii of curved portions of FIG. 30.

The roller assemblies 108 and parts thereof are illustrated in detail in FIGS. 6-31. Each roller assembly 108 has a generally cylindrical shell 130 of a non-magnetic material (for example aluminium) inside of which is disposed an array of lens-shaped magnets 132 disposed generally axially thereallong.

"Non-magnetic" as used herein is intended to refer to a material which doesn't significantly interfere with the magnetic field associated with the magnets 132.

The array of magnets 132 generally comprises two arrangements. A first arrangement 134 is a radially disposed "seed of life" pattern as shown in FIG. 8.

A second arrangement 136 generally comprises six magnets equidistantly spaced about the rotational axis 104 of the roller 102 in a generally conical layout. In other words, one end of each of the magnets 132 is closer to the rotational axis 138 than is its opposite end. Hence the magnets 132 of the second arrangement 136 either converge or diverge relative to the rotational axis 138 (depending on one's frame of reference).

A second arrangement 136 is located adjacent each first arrangement with the magnets 132 of each second arrangement 136 being closest to the rotational axis 104 adjacent the first arrangement 134. In other words, the magnets 132 of the second arrangement 136 diverge from the rotational axis 104 away from the adjacent first arrangement 134.

As can be seen in FIGS. 9 through 16, each of the magnets 132 of each second arrangement 136 has a slightly different orientation than the remaining magnets 132 of the second arrangement 136. As mentioned above, each magnet 132 has a generally lens-like shape in that it has generally parallel planar side faces 140 and curved front and rear faces 142 which meet at opposite edges 144 as can be seen in FIG. 9A. A lens axis 146 extends through each lens 132 between the edges 144 equidistant from the side faces 140.

Each lens 132 in the second arrangement 136 is oriented as if it has been rotated about 30° (thirty degrees) about its lens axis 146 relative to the immediately adjacent lenses 132. The arrow indicated by reference 148 in FIG. 9A illustrates the rotation. FIGS. 12 through 14 and 15 through 18 illustrate the resulting orientations. Note for example that one of the two lenses 132 apparent in FIG. 12 (to the left as illustrated) presents its side face parallel to the plane of the page whereas the other (to the right as illustrated) has its side faces 140 perpendicular to the plane of the page. FIG. 16 illustrates the reverse arrangement.

The magnets 132 are held in their respective positions by respective 18 magnet and 6 magnet holders 150 and 152. FIGS. 10 through 14 and 24 through 31 illustrate the former and FIGS. 15 through 23 illustrate the latter. Quite simply the magnet holders 150 and 152 are non-magnetic blocks with suitable recesses for receiving the magnets 132 to align and hold them in their desired positions.

The 18 magnet holders 150 hold both a first arrangement 134 and a second arrangement 136 of magnets 132. The 6 magnet holders 152 hold only a second arrangement 136 of magnets. It should be borne in mind that the magnet holders 150 and 152 are merely exemplary as no doubt other securement means are viable. For example the entire array could be cast into a suitable potting material such as a thermosetting or thermal setting polymer or a chemically setting resin such as epoxy.

Reference is now made to FIGS. 20 through 23 illustrating a six magnet holder 152. The 6 magnet holder 152 has a generally cylindrical body 160 having a plurality of recesses 162 each of which accommodates a single magnet 132.

Each of the recesses 162 is configured to receive its respective magnet in a desired orientation by closely engaging the side faces 140 of the magnet 132.

Locating holes 164 are provided between opposite faces 166 of the 6 magnet holder 152 to align with locating rods or bolts 168 (see FIG. 6) which extend through the roller assembly 102. The locating holes 164 align the magnet holders 150 and 152 and secure the magnet holders 150 and 152 to the balance of the roller assemblies for rotation therewith.

Reference is now made to FIGS. 24 through 31 which illustrate 18 magnet holders 150. The 18 magnet holders are similar to the 6 magnet holders on one side but, on the opposite side, include further recesses 170 for receiving and holding the magnets 132 of the first arrangement 134. As with the 6 magnet holder 152, locating holes 164 are provided to align with locating rods or bolts 168 and retain the 18 magnet holder 150 in a desired orientation within the roller assembly 104.

In use, the motor 108 is activated to rotate the roller assemblies 102 via the drive belt 112. The desired speed at which the rollers 102 rotate may vary depending upon the purpose for which the resonator is to be used. For example, it is believed that running the roller assemblies 102 at 3,500 to 4,000 rpm may prove to be beneficial in water purification applications.

Use of the resonator 100 doesn't require that the object to be treated surround the roller assemblies 102. Being adjacent thereto is generally sufficient and accordingly, in the case of fluids all that is required is that a non-magnetic conduit for the fluid pass by the resonator 100. It is believed that purification time will depend on the substance being purified and the overall size of the resonator 100. For water purification using a resonator 100 having rollers of about 17 inches in length and about 4 inches in diameter it is believed that approximately 0.03 seconds would be required for killing a virus. PCB's may require about 20 minutes. Accordingly it should be apparent that a continuous flow operation (as contrasted with a batch operation) may be viable at least for some applications.

The above description focuses upon the use of a "seed of life" pattern. The seed of life is but one geometric pattern which incorporates the reoccurring ratios or sequences found in nature which are collectively referred to as "sacred geometry". It is believed that the inherent ratios of the sacred geometry associated with the "seed of life" has a strong influence on the effectiveness of the resulting magnetic field. Accordingly, it stands to reason that beneficial results would also be achieved by selecting other of the geometric patterns within the sacred geometry group.

The magnets 132 should be as strong as reasonably possible. Accordingly rare earth magnets are presently preferred in view of their high strength to size ratio. Whilst this is a preference it is not a requirement. Other forms of permanent magnets or even electromagnets may be used. Preferably the magnets 132 are symmetrically disposed to minimize rotationally induced vibration during use. The magnets are preferably arranged in alternating north-south orientation, but this may be changeable.

The resonator 100 of the present invention is believed to have practical application as a means to purify water or food by killing pathogens and breaking down toxins. The resonator 100 also may have practical application in direct application to a human body and animals to assist in restoring circulation, treating inflammation, ulceration, viral and bacterial infections and as a general tonic. The resonator 100 may also be useful for reducing environmental toxins in air, water, food and soil. Preliminary tests are believed to be able to show the breakdown of toxic compounds (such as in automobile exhaust) into smaller and less harmful constituent elements such as IC, CO, NO and $SO_2$.

The above invention is described in an illustrative rather than a restrictive sense. Variations may be apparent to persons skilled in such arrangements without departing from the spirit and scope of the invention as defined by the claims set out below.

PARTS LIST 100 resonator
102 roller assembly
104 axis (roller assembly)
106 common axis (of roller assemblies)
108 motor
110 driven pulleys
112 drive belt
114 drive pulleys
120 base
122 support plates
124 adjustable motor mount
130 shell (roller)
132 magnets
134 first arrangement (seed of life)
136 second arrangement (conical)

138 rotational axis (roller assembly)
140 side face (lens)
142 front and rear faces (lens)
144 edges (lens)
146 lens axis
148 arrows (showing rotational displacement of lens)
150 18 magnet holder
152 6 magnet holder
162 recesses (for holding magnets)
164 locating holes
166 opposite faces (of body)
168 rods or bolts (extending through roller assembly)
170 recesses in 150 for holding first arrangement of magnets

The invention claimed is:

1. A magnetic resonator comprising: a support structure; a plurality of roller assemblies mounted to said support structure for rotation about respective axes of rotation which are generally parallel to one another; drive means coupled to said roller assemblies for rotating each of said roller assemblies about its respective axis of rotation relative to said support structure; each said roller assembly housing a plurality of magnets disposed along said respective axes; said plurality of magnets are grouped in a plurality of a first and second arrangements in distinct, non-identical patterns, with a first arrangement being interspersed between a pair of said second arrangements; at least one of said first and second arrangements incorporating a pattern or shape based on a seed of life pattern.

2. The magnetic resonator of claim 1 wherein: said second arrangement of magnets includes a plurality of said magnets disposed generally equidistantly about said respective axes of rotation in a generally pyramid or cone-shaped pattern or shape with a vertex of said pyramid or cone facing said first arrangement.

3. The magnetic resonator of claim 2 wherein: said magnets in said second arrangement of magnets have discernible front and rear faces on opposite sides of a longitudinal axis; said magnets are arranged with said longitudinal axes lying along said pyramid or cone shape; each said magnet is rotated by an equal amount in a common direction from its neighbour whereby diametrically opposed magnets have respective of said front and rear faces facing in generally perpendicular directions.

4. The magnetic resonator of claim 3 wherein: said magnets in said first and second arrangements have generally planar side faces joined by curved front and rear faces which meet at opposite ends to present a lens-like profile when viewed from the said front or rear faces and a generally rectangular profile when reviewed from said side faces; and, said longitudinal axis of each said lens extends through said ends.

5. The magnetic resonator of claim 4 wherein: said magnets are mounted in support blocks having recesses formed therein for receiving and orienting said magnets.

6. The magnetic resonator of claim 5 wherein: said support blocks are cylindrical; said roller assemblies have a tubular shell of a non-magnetic material housing said support blocks; and, retainers are provided which act between said shell and said support blocks to constrain said support blocks against rotation relative to said shell.

7. The magnetic resonator of claim 6 further comprising: three of said roller assemblies spaced equidistantly about a common axis.

8. The magnetic resonator of claim 7 wherein at least some of said magnets are arranged with their respective north and south poles alternating.

9. The magnetic resonator of claim 8 further comprising: four of said first arrangements and nine of said second arrangements, along each said roller.

10. The magnetic resonator of any one of claim 1 wherein each said second arrangement has six (6) magnets.

11. The magnetic resonator of claims 1 wherein said drive means is arranged to rotate said rollers at from 3,500 to 4,000 revolutions per minute ("rpm").

\* \* \* \* \*